(12) United States Patent
Velikov (10) Patent No.: US 8,808,292 B2
(45) Date of Patent: Aug. 19, 2014

(54) ORTHOPEDIC SCREW

(75) Inventor: Jordan Velikov, Thalwil (CH)

(73) Assignee: Zimmer GmbH, Winterthur (CH)

( * ) Notice: Subject to any disclaimer, the term of this patent is extended or adjusted under 35 U.S.C. 154(b) by 1114 days.

(21) Appl. No.: 12/268,498

(22) Filed: Nov. 11, 2008

(65) Prior Publication Data

US 2010/0121327 A1    May 13, 2010

(51) Int. Cl.
  *A61B 17/76*  (2006.01)
  *A61B 17/86*  (2006.01)
  *A61B 17/72*  (2006.01)
  *A61B 17/74*  (2006.01)

(52) U.S. Cl.
  CPC .............. *A61B 17/863* (2013.01); *A61B 17/725* (2013.01); *A61B 17/744* (2013.01); *A61B 17/8635* (2013.01)
  USPC ........................................................ 606/64

(58) Field of Classification Search
  CPC ............................. A61B 17/725; A61B 17/744
  USPC ...................................... 606/62–68
  See application file for complete search history.

(56) References Cited

U.S. PATENT DOCUMENTS

| | | | |
|---|---|---|---|
| 570,786 A | 11/1896 | Church | |
| 2,177,003 A * | 10/1939 | Purtell | 411/301 |
| 2,243,717 A | 5/1941 | Godoy | |
| 3,433,220 A | 3/1969 | Zickel | |
| 3,882,917 A * | 5/1975 | Orlomoski | 411/309 |
| 4,048,898 A | 9/1977 | Salter | |
| 4,219,015 A | 8/1980 | Steinemann | |
| 4,408,601 A | 10/1983 | Wenk | |
| 4,576,534 A * | 3/1986 | Barth et al. | 411/412 |
| 4,733,654 A | 3/1988 | Marino | |
| 4,827,917 A | 5/1989 | Brumfield | |
| 4,838,252 A | 6/1989 | Klaue | |
| 4,959,064 A | 9/1990 | Engelhardt | |
| 5,032,125 A | 7/1991 | Durham et al. | |
| 5,041,114 A | 8/1991 | Chapman et al. | |
| 5,176,681 A | 1/1993 | Lawes et al. | |
| 5,242,447 A | 9/1993 | Borzone | |
| 5,304,180 A | 4/1994 | Slocum | |
| 5,387,214 A | 2/1995 | Kropf et al. | |
| 5,505,734 A | 4/1996 | Caniggia et al. | |
| 5,507,211 A | 4/1996 | Wagner | |
| 5,578,035 A | 11/1996 | Lin | |
| 5,601,553 A | 2/1997 | Trebing et al. | |
| 5,676,667 A | 10/1997 | Hausman | |
| 5,709,686 A | 1/1998 | Talos et al. | |

(Continued)

FOREIGN PATENT DOCUMENTS

| | | |
|---|---|---|
| DE | 4343117 A1 | 6/1995 |
| DE | 19518194 C2 | 11/1996 |

(Continued)

OTHER PUBLICATIONS

Surgical Technique—Zimmer ITST Intertrochanteric/Subtrochanteric Fixation System, 97-2257-102-01 Rev. 1 5MM 2005 Zimmer, Inc.

(Continued)

*Primary Examiner* — Ellen C Hammond
(74) *Attorney, Agent, or Firm* — Schwegman Lundberg & Woessner, P.A.

(57) ABSTRACT

An orthopedic screw that may be used to align and stabilize a bone fracture and a method for using the same.

19 Claims, 4 Drawing Sheets

(56) References Cited

U.S. PATENT DOCUMENTS

| | | |
|---|---|---|
| 5,779,705 A | 7/1998 | Matthews |
| 5,871,486 A * | 2/1999 | Huebner et al. ............... 606/305 |
| 5,904,683 A | 5/1999 | Pohndorf et al. |
| 5,947,733 A | 9/1999 | Sutter et al. |
| 6,004,324 A | 12/1999 | Gahr et al. |
| 6,046,560 A | 4/2000 | Lu et al. |
| 6,098,480 A | 8/2000 | Fleytman |
| 6,129,730 A | 10/2000 | Bono et al. |
| 6,206,881 B1 | 3/2001 | Frigg et al. |
| 6,235,031 B1 | 5/2001 | Hodgeman et al. |
| 6,331,179 B1 | 12/2001 | Fried et al. |
| 6,344,042 B1 | 2/2002 | Curtis et al. |
| 6,423,066 B1 | 7/2002 | Harder et al. |
| 6,461,360 B1 | 10/2002 | Adam |
| 6,533,789 B1 | 3/2003 | Hall, IV et al. |
| 6,550,567 B2 | 4/2003 | Murakami et al. |
| 6,565,573 B1 * | 5/2003 | Ferrante et al. ................. 606/62 |
| 6,623,486 B1 | 9/2003 | Weaver et al. |
| 6,645,209 B2 | 11/2003 | Hall, IV et al. |
| 6,648,889 B2 | 11/2003 | Bramlet et al. |
| 6,656,184 B1 | 12/2003 | White et al. |
| 6,705,176 B2 | 3/2004 | Ishii et al. |
| 6,719,759 B2 | 4/2004 | Wagner et al. |
| 6,769,507 B2 | 8/2004 | Murakami et al. |
| 6,835,197 B2 | 12/2004 | Roth et al. |
| 6,860,829 B2 | 3/2005 | Bock et al. |
| 7,883,509 B2 * | 2/2011 | Ferrante et al. ................. 606/64 |
| 2002/0045900 A1 | 4/2002 | Harder et al. |
| 2002/0072748 A1 | 6/2002 | Robioneck |
| 2002/0151898 A1 | 10/2002 | Sohngen et al. |
| 2003/0040747 A1 | 2/2003 | Dean et al. |
| 2003/0069581 A1 | 4/2003 | Stinson et al. |
| 2004/0059335 A1 | 3/2004 | Weaver et al. |
| 2004/0116930 A1 | 6/2004 | O'Driscoll et al. |
| 2004/0127898 A1 | 7/2004 | Adam |
| 2004/0138662 A1 | 7/2004 | Landry et al. |
| 2004/0260291 A1 | 12/2004 | Jensen |
| 2005/0011320 A1 | 1/2005 | Hsien |
| 2005/0015089 A1 | 1/2005 | Young et al. |
| 2005/0101958 A1 | 5/2005 | Adam |
| 2005/0161277 A1 | 7/2005 | Bock et al. |
| 2006/0058797 A1 | 3/2006 | Mathieu et al. |
| 2006/0095039 A1 | 5/2006 | Mutchler |
| 2006/0106384 A1 * | 5/2006 | Reber et al. ..................... 606/62 |
| 2006/0106386 A1 * | 5/2006 | Reber et al. ..................... 606/65 |
| 2006/0106389 A1 * | 5/2006 | Reber et al. ..................... 606/72 |
| 2008/0147066 A1 | 6/2008 | Longsworth |
| 2008/0147128 A1 | 6/2008 | Fritzinger |
| 2008/0234749 A1 | 9/2008 | Forstein |
| 2009/0264937 A1 | 10/2009 | Parrott |

FOREIGN PATENT DOCUMENTS

| | | |
|---|---|---|
| DE | 29620327 U1 | 3/1998 |
| DE | 19723339 A1 | 12/1998 |
| DE | 29823113 U1 | 5/2000 |
| DE | 19942252 A1 | 11/2000 |
| DE | 10051306 A1 | 4/2002 |
| DE | 10114906 A1 | 10/2002 |
| EP | 0172130 A2 | 2/1986 |
| EP | 1053718 A1 | 11/2000 |
| EP | 1214914 A2 | 6/2002 |
| EP | 1656899 A1 | 5/2006 |
| EP | 1759649 A1 | 7/2007 |
| JP | 2000-43739 | 2/2000 |
| WO | WO 99/11502 A1 | 3/1999 |
| WO | WO 99/35989 A1 | 7/1999 |
| WO | WO 99/65758 A1 | 12/1999 |
| WO | WO 2007/079814 A1 | 7/2004 |
| WO | WO 2004/066855 A1 | 8/2004 |
| WO | WO 2004/084701 A1 | 10/2004 |
| WO | WO 2006/076729 A2 | 7/2006 |

OTHER PUBLICATIONS

Product Brochure—Zimmer Sirus Intramedullary Nail System, 97-2290-001-00 5ML 2005 Zimmer, Inc.

Webpage—Zimmer Products, Intrasys Proximal Femur Intramedullary Nail, http://www.zimmer-orthopedics.com/VGP/en/Products/Fracture_Care/Intrasys/Intrasys?start=1&ArtId=(1 of 3) Sep. 17, 2008.

Operative Technique—Stryker Gamma3 Trochanteric Nail 180, 48 pp, 2006 Stryker.

Kapelevich, Alexander "Geometry and design of involute spur gears with asymmetric teeth", Mechanism and Machine Theory, vol. 35, Issue 1, Jan. 2000, pp. 117-130.

Kapelevich, Alexander and McNamara, Thomas "Direct Gear Design", Society of Manufacturing Engineers, Oct. 2003.

The International Search Report and Written Opinion mailed Jan. 27, 2010 in the related International Application No. PCT/EP2009/007058.

Manual der Osteosythese (five pages that include p. IV, an unnumbered page, pp. 140-141 and an unnumbered page) (Osteosythese) 1991.

* cited by examiner

FIG_6

FIG_7

FIG_8

ORTHOPEDIC SCREW

BACKGROUND

1. Field of the Invention

The present invention relates to orthopedic components. More particularly, the present invention relates to an orthopedic screw and to a method for using the same.

2. Description of the Related Art

An orthopedic assembly may be used to align and stabilize a fracture of a long bone. For example, to align and stabilize a fractured femur, the orthopedic assembly may include an intramedullary nail configured to be driven into a prepared intramedullary canal of the femur. The intramedullary nail of the orthopedic assembly may include bores that receive screws or other attachment devices for securing the intramedullary nail to the bone. To stabilize opposing portions of the fractured bone, the intramedullary nail itself may extend across a fracture line of the femur. Additionally, an orthopedic screw extending from the intramedullary nail may extend across a fracture line of the femur. For example, if the fracture line is located between the femoral shaft and the femoral head, an orthopedic screw may extend through a bore of the intramedullary nail and into the head of the femur.

During the life of the implanted orthopedic assembly, an orthopedic screw may deviate from its proper position relative to the intramedullary nail. For example, the orthopedic screw may retract laterally from the femur. As another example, the orthopedic screw may migrate medially through the femoral head and into the pelvic cavity. As yet another example, the femoral head and/or the femoral neck may collapse relative to the femoral shaft.

SUMMARY

The present invention provides an orthopedic screw that may be used to align and stabilize a bone fracture, for example.

According to an embodiment of the present invention, an orthopedic screw is provided that includes a distal end, a proximal end, a shaft, and a thread. The shaft extends between the distal end and the proximal end of the orthopedic screw and includes a longitudinal axis. The thread extends helically from the shaft to define a plurality of teeth, each of the plurality of teeth being separated by a root. Each of the plurality of teeth includes a leading flank facing the distal end of the orthopedic screw, a trailing flank facing the proximal end of the orthopedic screw, and a crest extending between the leading flank and the trailing flank, the crest extending transversely to the longitudinal axis of the shaft.

According to another embodiment of the present invention, an orthopedic assembly is provided that is configured to repair a bone fracture. The orthopedic assembly includes an alignment device having a bore and an orthopedic screw sized to be received within the bore of the alignment device and configured to be driven into a bone. The orthopedic screw includes a distal end, a proximal end, a shaft, and a thread. The shaft extends between the distal end and the proximal end of the orthopedic screw and includes a longitudinal axis. The thread extends helically from the shaft to define a plurality of teeth, each of the plurality of teeth being separated by a root. Each of the plurality of teeth includes a leading flank facing the distal end of the orthopedic screw, a trailing flank facing the proximal end of the orthopedic screw, and a crest extending between the leading flank and the trailing flank, the crest extending transversely to the longitudinal axis of the shaft.

According to yet another embodiment of the present invention, a method is provided for implanting an orthopedic screw. The method includes the step of providing access to a bone of a joint, the bone configured to receive a load from the joint along a first direction. The method also includes the step of providing an orthopedic screw having a distal end, a proximal end, a shaft extending between the distal end and the proximal end, and a thread extending helically from the shaft to define a plurality of teeth, and each of the plurality of teeth including a leading flank facing the distal end of the orthopedic screw, a trailing flank facing the proximal end of the orthopedic screw, and a crest extending between the leading flank and the trailing flank. The method also includes the step of implanting the orthopedic screw into the bone such that at least a portion of the crests of the plurality of teeth extend in a second direction essentially perpendicular to the first direction of the load.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

Corresponding reference characters indicate corresponding parts throughout the several views. The exemplifications set out herein illustrate exemplary embodiments of the invention and such exemplifications are not to be construed as limiting the scope of the invention in any manner.

DETAILED DESCRIPTION

Figure 1:
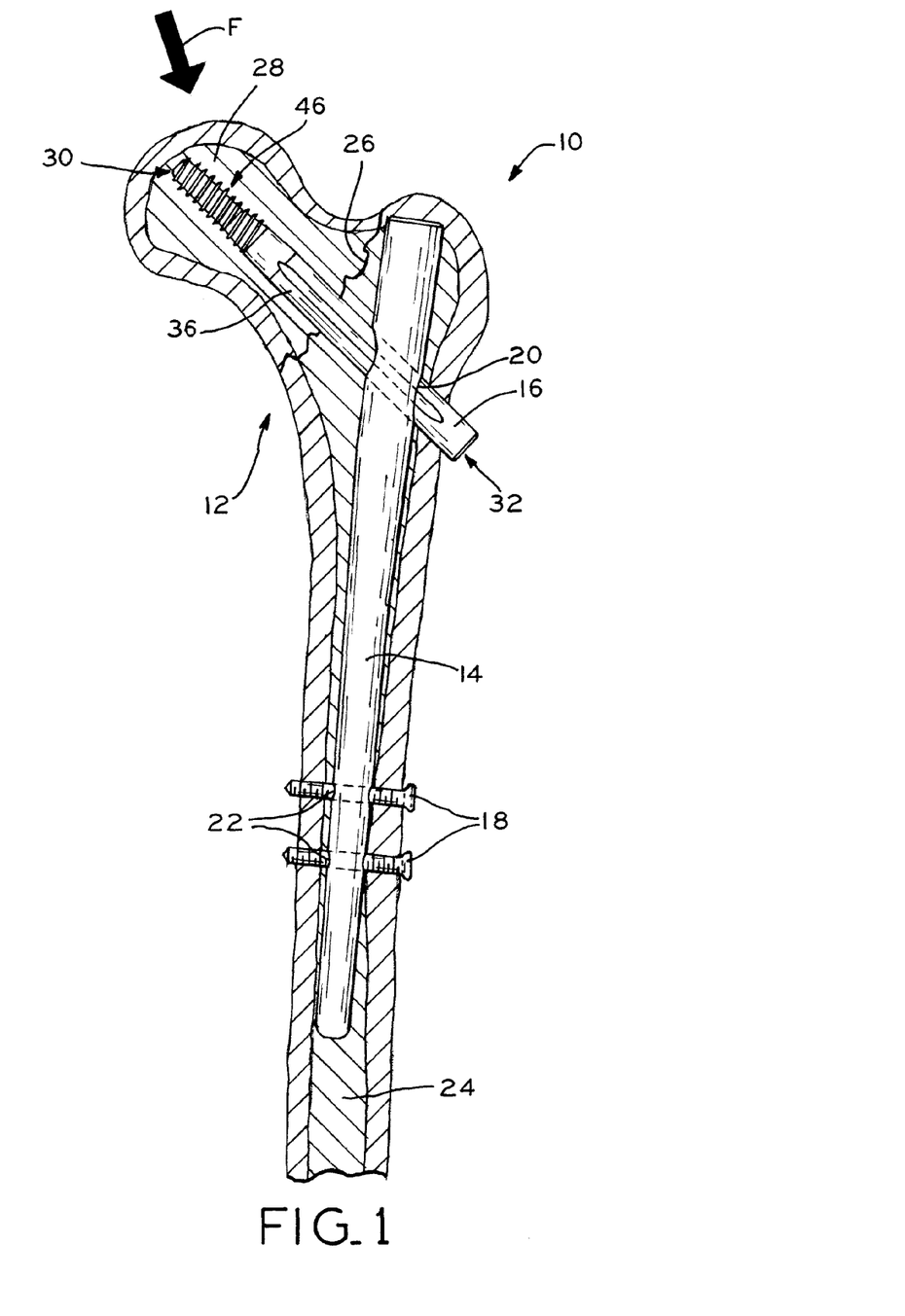
FIG. 1 is a cross-sectional view of a femur with an orthopedic assembly including an orthopedic screw of the present invention implanted therein.

Referring to FIG. 1, orthopedic assembly 10 is shown implanted into femur 12. Although orthopedic assembly 10 is described and depicted herein as being implanted into femur 12, orthopedic assembly 10 may be used in other long bones of the body, such as the tibia, fibula, radius, ulna, clavicle, and other long bones. Orthopedic assembly 10 includes intramedullary nail 14, orthopedic screw or lag screw 16, and distal screws 18. Although orthopedic assembly 10 is described and depicted herein as including intramedullary nail 14, orthopedic assembly 10 may include other alignment devices such as a compression plate, a plate for a dynamic hip system, or a similar alignment device.

Intramedullary nail 14 of orthopedic assembly 10 includes transverse bore 20 for receiving orthopedic screw 16 and distal bores 22 for receiving distal screws 18. During surgery, intramedullary nail 14 is implanted into prepared intramedullary canal 24 of femur 12. To prevent rotation and removal of intramedullary nail 14, a surgeon implants distal screws 18 into femur 12 through distal bores 22 of intramedullary nail 14. To secure intramedullary nail 14 within intramedullary canal 24 of femur 12, the surgeon implants orthopedic screw 16 into femur 12 through transverse bore 20 of intramedullary nail 14. As shown in FIG. 1, orthopedic screw 16 may extend across fracture 26 in femur 12. For example, in cases of a fracture or other trauma to femoral head 28, the surgeon may implant orthopedic screw 16 across fracture 26 and into femoral head 28 of femur 12. Depending on its location in femur 12, fracture 26 may be classified as a subcapital neck fracture, a transcervical neck fracture, or an intertrochanteric fracture, for example.

Referring still to FIG. 1, femoral head 28 of femur 12 forms part of a hip joint. Specifically, femoral head 28 of femur 12 articulates with an acetabulum of a pelvis (not shown). Femoral head 28 of femur 12 bears a load or a force from the pelvis in a direction indicated by arrow F. As shown in FIG. 1, arrow F extends downward upon femoral head 28 of femur 12 and at a transverse angle relative to intramedullary nail 14 located within femur 12.

Figure 4:
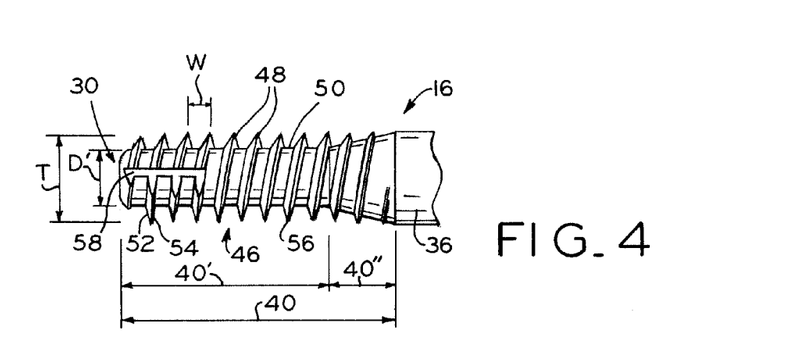
FIG. 4 is a partial plan view of the orthopedic screw of FIG. 1.
Figure 5:
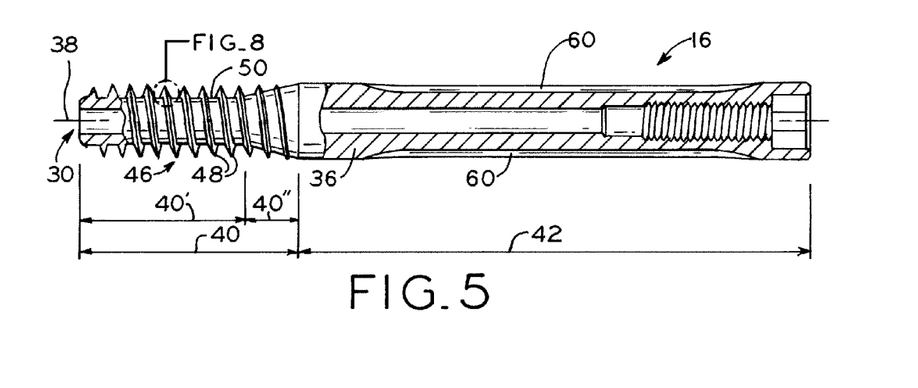
FIG. 5 is a partial cross-sectional view of the orthopedic screw of FIG. 4.
Figure 6:
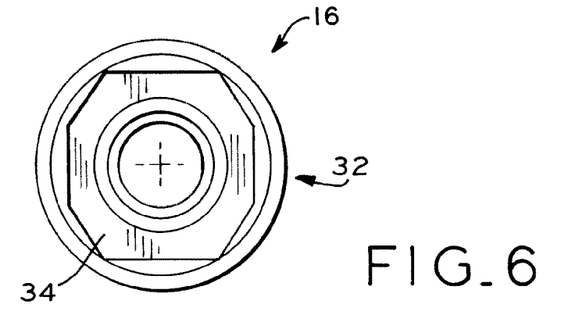
FIG. 6 is a proximal view of the orthopedic screw of FIG. 2 taken along line 6-6 of FIG. 2.

Referring next to FIGS. 1-6, orthopedic screw 16 includes distal end 30 and proximal end 32. As used herein, "proximal" and "distal" are determined relative to a surgeon or another user. Distal end 30 of orthopedic screw 16 is located away from the surgeon during implantation, because distal end 30 is implanted into femur 12 to fix orthopedic screw 16 to femur 12. Proximal end 32 of orthopedic screw 16 is located proximate the surgeon so that the surgeon is able to manipulate orthopedic screw 16 during implantation. As shown in FIG. 6, proximal end 32 of orthopedic screw 16 includes bore 34 that cooperates with a tool (not shown) for implanting orthopedic screw 16. Bore 34 may be octagonal, hexagonal, D-shaped, slotted, star-shaped, or another known shape, and configured to cooperate with a similarly shaped tool. Unlike a typical screw, proximal end 32 of orthopedic screw 16 lacks a head extending outwardly.

Figure 2:
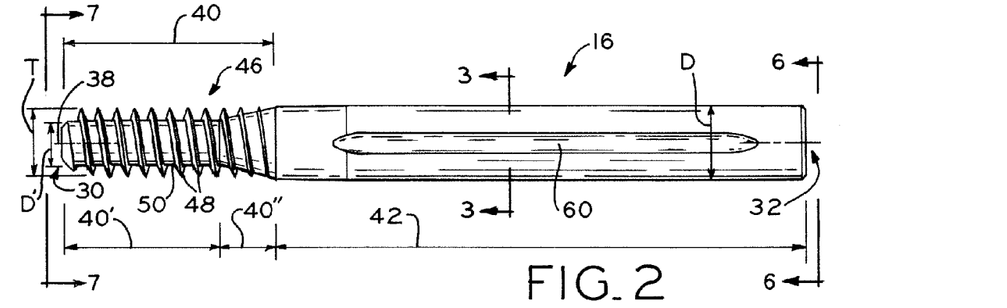
FIG. 2 is a radial elevational view of the orthopedic screw of FIG. 1.

Referring next to FIGS. 2-8, orthopedic screw 16 also includes shaft 36 extending between distal end 30 and proximal end 32. Shaft 36 includes longitudinal axis 38 extending therethrough. As shown in FIG. 2, shaft 36 is more narrow near distal end 30 of orthopedic screw 16 than near proximal end 32 of orthopedic screw 16. Shaft 36 includes tapered portion 40 near distal end 30 of orthopedic screw 16 and non-tapered portion 42 near proximal end 32 of orthopedic screw 16. Tapered portion 40 of shaft 36 may include narrow section 40' and ramp or expansion section 40". Narrow section 40' is portion of shaft 36 within tapered portion 40 having a constant outer diameter. Ramp section 40" is a portion of shaft 36 within tapered portion 40 that gradually widens until reaching non-tapered portion 42. It is within the scope of the present invention that ramp section 40" may extend entirely across tapered portion 40 of shaft 36.

Orthopedic screw 16 may be provided in various dimensions to accommodate patients having bones of various dimensions. For example, the length of shaft 36, or the distance between distal end 30 and proximal end 32 of orthopedic screw 16, may be as small as approximately 60 millimeters (mm), 70 mm, 80 mm, or 90 mm, or as large as approximately 100 mm, 110 mm, 120 mm, or 130 mm. As another example, outer diameter D of non-tapered portion 42 of shaft 36 near proximal end 32 of orthopedic screw 16 may be as small as approximately 9.0 mm, 9.5 mm, or 10.0 mm, or as large as approximately 10.5 mm, 11.0 mm, 11.5 mm, or more. As yet another example, outer diameter D' of narrow section 40' of shaft 36 within tapered portion 40 may be as small as approximately 5.0 mm, 5.5 mm, or 6.0 mm, or as large as approximately 6.5 mm, 7.0 mm, 7.5 mm, or more.

Orthopedic screw 16 may be constructed of any rigid, biocompatible material. For example, orthopedic screw 16 may be constructed of a biocompatible ceramic or metal including, but not limited to, titanium, stainless steel, cobalt chromium, cobalt chromium molybdenum, or alloys thereof.

Referring to FIG. 4, orthopedic screw 16 further includes thread 46 that extends helically from shaft 36. Thread 46 forms multiple teeth 48 that extend from shaft 36 and may be configured to tap bone of femur 12 (FIG. 1). Specifically, each 360 degree turn of thread 46 around shaft 36 forms an independent tooth 48, so multiple 360 degree turns of thread 46 around shaft 36 form multiple teeth 48. Advantageously, thread 46 is configured to remove a minimum quantity of bone from femur 12 while providing adequate surface area to maintain contact between thread 46 and the bone after implantation of orthopedic screw 16. Also advantageously, thread 46 is configured to minimize the necessary starting load and insertion torque required to implant orthopedic screw 16.

According to an exemplary embodiment of the present invention, thread 46 maintains a constant pitch across shaft 36. Adjacent teeth 48 are separated by a portion of shaft 36 referred to herein as root 50. To maintain a constant pitch, adjacent teeth 48 may be separated by roots 50 of the same size. For example, width W of root 50 may be as small as approximately 1.0 mm, 1.5 mm, 2.0 mm, or 2.5 mm, or as large as approximately 3.0 mm, 3.5 mm, 4.0 mm, or more. It is within the scope of the present invention that adjacent teeth 48 may be separated by roots 50 of different sizes.

According to another exemplary embodiment of the present invention, thread 46 maintains a constant outer diameter T across shaft 36. As shown in FIG. 2, thread 46 may extend entirely across tapered portion 40 of shaft 36, including both narrow section 40' and ramp section 40". Across narrow section 40' of shaft 36 having a constant outer diameter D', thread 46 may maintain a constant height, which is measured from root 50 in a direction perpendicular to longitudinal axis 38 of shaft 36. For example, the height of thread 46 may be as small as approximately 1.0 mm, 1.5 mm, 2.0 mm, or as large as approximately 2.5, 3.0 mm, or more. Across ramp section 40" of increasing shaft 36 diameter, the height of thread 46 may decrease by a corresponding amount to maintain a constant outer diameter T of thread 46.

According to yet another exemplary embodiment of the present invention, orthopedic screw 16 maintains a constant outer diameter across its entire length. In other words, outer diameter T of thread 46 may be the same as the outer diameter of an unthreaded region of shaft 36. As shown in FIG. 2, outer diameter T of thread 46 is essentially the same as outer diameter D of non-tapered portion 42 of shaft 36. Orthopedic screw 16 may have an outer diameter across its length as small as approximately 9.0 mm, 9.5 mm, or 10.0 mm, or as large as approximately 10.5 mm, 11.0 mm, 11.5 mm, or more, for example.

Figure 8:
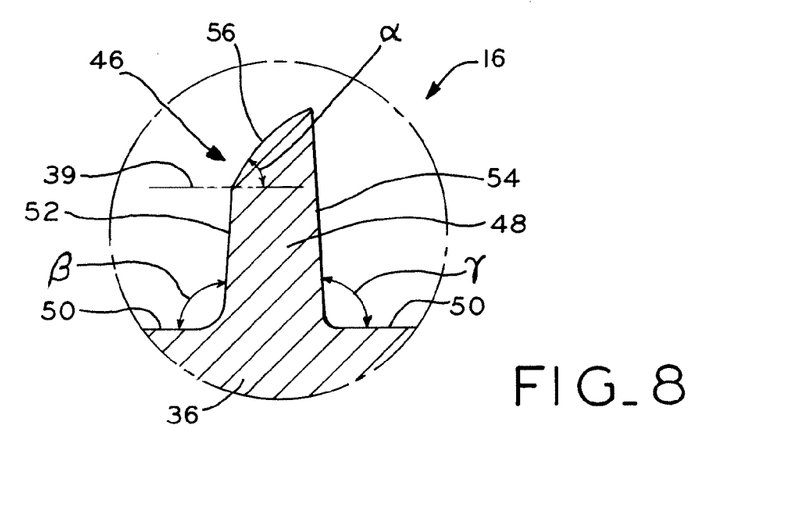
FIG. 8 is a partial cross-sectional view of a tooth of the orthopedic screw of FIG. 5.

Referring to FIG. 8, each tooth 48 includes leading flank 52, trailing flank 54, and crest 56. Leading flank 52 of tooth 48 faces distal end 30 of orthopedic screw 16. Trailing flank 54 of tooth 48 is located opposite leading flank 52 of tooth 48 and faces proximal end 32 of orthopedic screw 16 (FIG. 2). The width of each tooth 48, or the distance between leading flank 52 and trailing flank 54, which is measured parallel to longitudinal axis 38 of shaft 36, may be as small as approximately 0.2 mm, 0.4 mm, or 0.6 mm, or as large as approximately 0.8 mm, 1.0 mm, 1.2 mm, or more, for example.

According to an exemplary embodiment of the present invention, an angle β is formed between an adjacent root 50 and leading flank 52 of tooth 48. For example, angle β between root 50 and leading flank 52 of tooth 48 may be as small as approximately 90 degrees, 95 degrees, or 100 degrees, or as large as approximately 105 degrees, 110 degrees, or more.

According to another exemplary embodiment of the present invention, an angle γ is formed between an adjacent root 50 and trailing flank 54 of tooth 48. For example, angle γ between root 50 and trailing flank 54 of tooth 48 may be as small as approximately 90 degrees, 92 degrees, 95 degrees, or 100 degrees, or as large as approximately 105 degrees, 110 degrees, or more.

Figure 9:
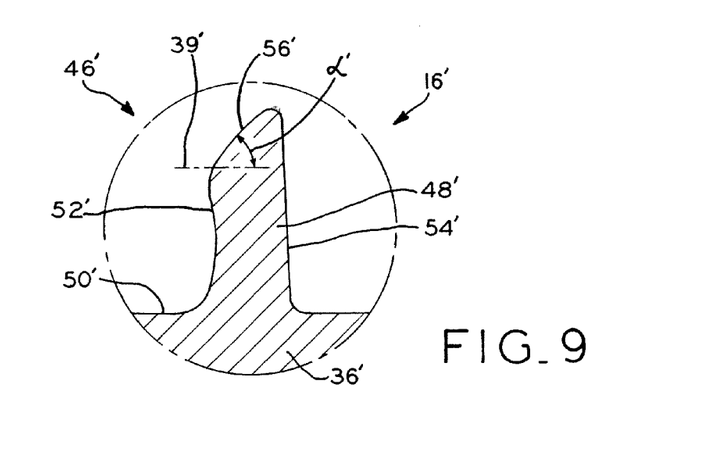
FIG. 9 is a partial cross-sectional view, similar to FIG. 8, of a tooth of another orthopedic screw of the present invention.

According to yet another exemplary embodiment of the present invention, leading flank 52' of tooth 48' may be slightly concave, as shown in FIG. 9. In other words, between shaft 36' and crest 56', leading flank 52' of tooth 48' may curve inward toward trailing flank 54' of tooth 48'. For example, leading flank 52' of tooth 48' may have a radius of curvature as small as approximately 5 mm, 10 mm, or 15 mm, or as large as approximately 20 mm, 25 mm, or more.

Referring again to FIG. 8, crest 56 extends between leading flank 52 and trailing flank 54 of tooth 48. Angle α is defined between crest 56 of tooth 48 and longitudinal axis 38 of shaft 36 (FIG. 5). If crest 56 is convex, angle α may be defined between a line tangent to the peak of curvature of crest 56 and longitudinal axis 38 of shaft 36. For purposes of illustration, axis 39 is shown next to tooth 48. Axis 39 extends parallel to longitudinal axis 38 of shaft 36, thus angle α between crest 56 and axis 39 is the same as angle α between crest 56 and longitudinal axis 38. An exemplary crest 56 of tooth 48 extends transversely to longitudinal axis 38 of shaft 36 (FIG. 5). Angle α between crest 56 of tooth 48 and axis 39 may range between 0 degrees and 90 degrees. For example, angle α between crest 56 of tooth 48 and axis 39 may be as small as approximately 10 degrees, 20 degrees, 30 degrees, or 40 degrees, or as large as approximately 50 degrees, 60 degrees, 70 degrees, 80 degrees, or more. Another exemplary crest 56 of tooth 48 extends parallel to longitudinal axis 38 of shaft 36 (FIG. 5). For example, as shown in FIG. 10, the angle between crest 56" of tooth 48" and axis 39" equals approximately 0 degrees.

Figure 10:
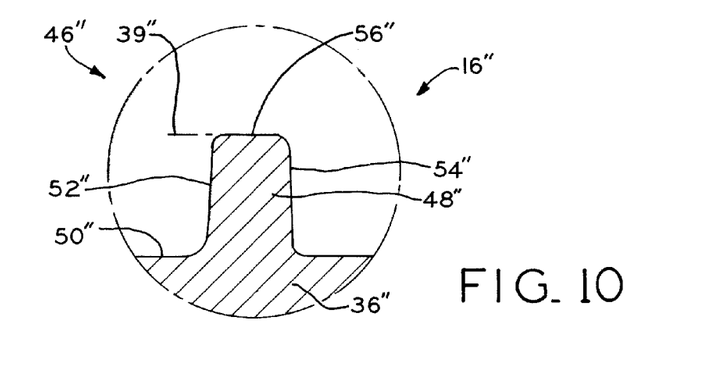
FIG. 10 is a partial cross-sectional view, similar to FIG. 8, of a tooth of yet another orthopedic screw of the present invention.
Figure 11:
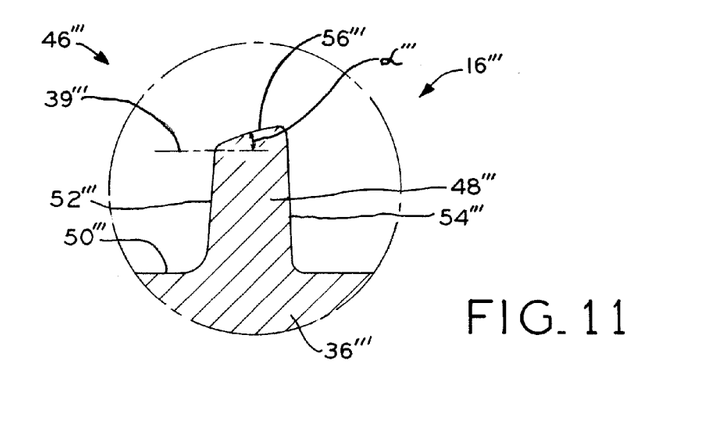
FIG. 11 is a partial cross-sectional view, similar to FIG. 8, of a tooth of still yet another orthopedic screw of the present invention.

According to an exemplary embodiment of the present invention, a set of orthopedic screws is provided, such as orthopedic screw 16 of FIG. 8, orthopedic screw 16' of FIG. 9, orthopedic screw 16" of FIG. 10, and orthopedic screw 16'" of FIG. 11. Each orthopedic screw of the set may form a unique angle α between crest 56 of tooth 48 and axis 39. For example, angle α' of FIG. 9 is greater than angle α of FIG. 8, which is greater than angle α'" of FIG. 11, which is greater than the angle of FIG. 10 (not labeled). As discussed below, a surgeon may select a desired orthopedic screw from the set provided.

According to another exemplary embodiment of the present invention, trailing flank 54 of tooth 48 extends further from shaft 36 than leading flank 52 of tooth 48 such that crest 56 faces distal end 30 of orthopedic screw 16, as shown in FIG. 4. Upon implantation into femur 12, trailing flank 54 of flank tooth 48 serves to prevent orthopedic screw 16 from retracting or pulling out of femur 12 (FIG. 1). It is also within the scope of the present invention that leading flank 52 of tooth 48 may extend further from shaft 36 than trailing flank 54 of tooth 48 such that crest 56 faces proximal end 32 of orthopedic screw 16.

According to yet another exemplary embodiment of the present invention, crest 56 of tooth 48 may be convex. In other words, between leading flank 52 and trailing flank 54 of tooth 48, crest 56 may curve away from longitudinal axis 38 of shaft 36. Crest 56 may have a radius of curvature as small as approximately 0.5 mm, 1.0 mm, or 1.5 mm, or as large as approximately 2.0 mm, 2.5 mm, 3.0 mm, or more.

Referring still to FIG. 8, tooth 48 may include chamfered or rounded edges. In an embodiment of the present invention, the tip of tooth 48 may be chamfered between leading flank 52 and crest 56 and/or between trailing flank 54 and crest 56. Providing chamfered edges of crest 56 may reduce the cutting aggressiveness of tooth 48, and as a result, may reduce the quantity of bone removed by thread 46 of orthopedic screw 16. Advantageously, reducing the quantity of bone removed by thread 46 may reduce the likelihood of orthopedic screw 16 retracting laterally from femur 12 or migrating medially through femur 12 (FIG. 1). In another embodiment of the present invention, the base of tooth 48 may be chamfered between leading flank 52 and root 50 and/or between trailing flank 54 and root 50. Providing chamfered edges between root 50 and tooth 48 may reduce the occurrence of stress risers in femur 12 (FIG. 1). These chamfered edges may have radii of curvature as small as approximately 0.01 mm, 0.1 mm, 1.0 mm, or more, for example.

Figure 7:
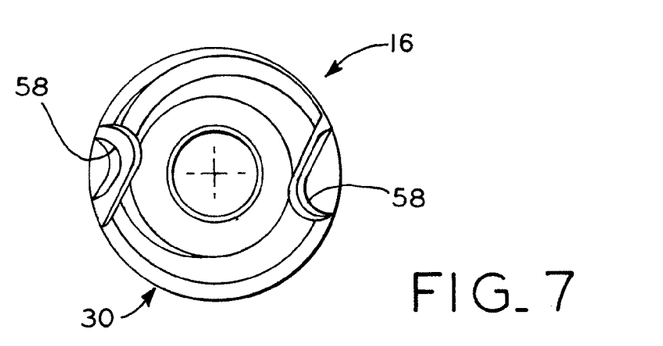
FIG. 7 is a distal view of the orthopedic screw of FIG. 2 taken along line 7-7 of FIG. 2.

Referring to FIGS. 4 and 7, orthopedic screw 16 further includes at least one cutting flute 58 in thread 46. Cutting flute 58 forms a recession or interruption in the periphery of thread 46. As shown in FIG. 7, cutting flute 58 forms a J-shaped recession in the periphery of thread 46. Cutting flute 58 may define a cutting surface and may convey debris away from orthopedic screw 16 during implantation. For this reason, cutting flute 58 may be formed by sharp, non-chamfered edges. If multiple cutting flutes 58 are provided, as shown in FIG. 7, cutting flutes 58 may be evenly spaced around the periphery of orthopedic screw 16.

According to an exemplary embodiment of the present invention, each cutting flute 58 interrupts less than the entire thread 46. For example, as shown in FIG. 4, cutting flute 58 begins near distal end 30 of orthopedic screw 16 and interrupts approximately three teeth 48 of thread 46 as it approached proximal end 32 of orthopedic screw 16.

According to another exemplary embodiment of the present invention, the depth of cutting flute 58, or the distance cutting flute 58 extends into thread 46, may vary across thread 46. For example, as shown in FIGS. 4 and 7, cutting flute 58 may decrease in depth from distal end 30 to proximal end 32 of orthopedic screw 16 (FIG. 5). Advantageously, cutting flute 58 may facilitate implantation of orthopedic screw 16 by providing for aggressive cutting into femur 12 (FIG. 1) by distal end 30 of orthopedic screw 16 while still limiting the total amount of bone removed by orthopedic screw 16.

Figure 3:
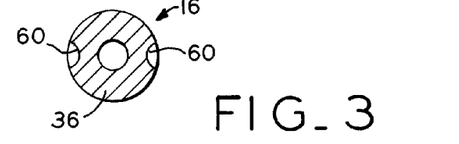
FIG. 3 is a cross-sectional view of the orthopedic screw of FIG. 2 taken along line 3-3 of FIG. 2.

Referring to FIGS. 2-5, orthopedic screw 16 further includes at least one glide flute 60 in shaft 36. Glide flute 60 forms a recession in the periphery of shaft 36. As shown in FIG. 3, glide flute 60 forms a semi-circular recession in the periphery of shaft 36. Glide flute 60 may be used to align orthopedic screw 16 with intramedullary nail 14. If multiple glide flutes 60 are provided, as shown in FIG. 3, glide flutes 60 may be evenly spaced around the periphery of orthopedic screw 16.

According to an exemplary embodiment of the present invention, glide flute 60 may be used to determine the relative position of cutting flute 58. For example, each glide flute 60 of orthopedic screw 16 illustrated in FIGS. 2-8 is spaced approximately 90 degrees from both cutting flutes 58. As discussed below, a surgeon may desire to orient cutting flute 58 within femur 12 relative to the load indicated by arrow F (FIG. 1).

Referring back to FIG. 1, a method is provided for repairing fracture 26 in femur 12. First, a surgeon accesses femur 12. Accessing femur 12 may involve surgically traversing soft tissue surrounding femur 12. As discussed above, femur 12 articulates with a pelvis (not shown) to form the hip joint, and femur 12 bears a load from the pelvis in the direction indicated by arrow F.

Next, the surgeon prepares intramedullary canal 24 of femur 12 and implants intramedullary nail 14 into the prepared intramedullary canal 24. Preparing intramedullary canal 24 of femur 12 may involve reaming and/or rasping intramedullary canal 24 with a tool having a profile congruent to the shape of intramedullary nail 14. To prevent rotation and loosing of intramedullary nail 14 within intramedullary canal 24 of femur 12, the surgeon may screw distal screws 18 into femur 12 through distal bores 22 of intramedullary nail 14.

Finally, to stabilize fracture 26, the surgeon implants orthopedic screw 16 into femur 12. As shown in FIG. 1, orthopedic screw 16 extends through transverse bore 20 of intramedullary nail 14, across fracture 26, and into femoral head 28 of femur 12.

According to an exemplary embodiment of the present invention, orthopedic screw 16 is aligned in femur 12 such that crests 56 of teeth 48 located proximate the hip joint face arrow F and are oriented essentially perpendicular to arrow F. Advantageously, the force or load imparted on each tooth 48 of orthopedic screw 16 may be evenly dispersed across the surface of crest 56 rather than being concentrated onto an edge of tooth 48. By efficiently dispersing the force or load across crests 56 of orthopedic screw 16, the stress between orthopedic screw 16 and femoral head 28 of femur 12 may be reduced. As a result, the present invention may reduce the likelihood of femoral head 28 collapsing from femur 12.

To implant orthopedic screw 16, the surgeon first determines the orientation of shaft 36 of orthopedic screw 16 in the bone. Factors such as the shape of the bone itself, the type of alignment device being utilized, and/or the location of the injury, may determine the appropriate orientation of shaft 36. For example, as shown in FIG. 1, shaft 36 of orthopedic screw 16 is oriented transversely to intramedullary canal 24 of femur 12 and extends across fracture 26 and into femoral head 28. After the alignment of shaft 36 is determined, the surgeon selects an appropriate orthopedic screw 16 from a set. As mentioned above, the set may include various orthopedic screws 16, each providing a unique orientation of crest 56 relative to longitudinal axis 38 of shaft 36. The appropriate orthopedic screw 16 will provide crests 56 of teeth 48 that face arrow F and that are oriented essentially perpendicular to arrow F. For example, as shown in FIG. 1, longitudinal axis 38 of shaft 36 is angled acutely relative to arrow F. Therefore, the appropriate orthopedic screw 16 includes crests 56 that extend transversely to longitudinal axis 38 of shaft 36. As another example, if shaft 36 were aligned perpendicular to arrow F, such as if shaft 36 were inserted perpendicular to intramedullary canal 24 of femur 12, appropriate orthopedic screw 16 may include crests 56 that extend parallel to longitudinal axis 38 of shaft 36.

If orthopedic screw 16 is provided with cutting flute 58 in thread 46, implanting orthopedic screw 16 may involve rotating orthopedic screw 16 in femur 12 until cutting flute 58 faces away from arrow F. Specifically, teeth 48 that are not interrupted by cutting flute 58 should face arrow F. This alignment ensures that perpendicular crests 56 are aligned to receive the load from the joint along arrow F rather than a sharp, uneven cutting flute 58. As mentioned above, the surgeon may determine the location of cutting flute 58 based on the location of glide flute 60.

While this invention has been described as having preferred designs, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopedic screw comprising:
   a distal end;
   a proximal end;
   a shaft extending between the distal end and the proximal end of the orthopedic screw, the shaft comprising a longitudinal axis; and
   a thread extending helically from the shaft to define a plurality of teeth, each of the plurality of teeth being separated by a root, and each of the plurality of teeth comprising:
      a leading flank facing the distal end of the orthopedic screw;
      a trailing flank facing the proximal end of the orthopedic screw; and
      a crest extending between the leading flank and the trailing flank, the crest extending transversely to the longitudinal axis of the shaft, wherein each crest faces the distal end of the orthopedic screw, wherein the trailing flank extends further from the root than the leading flank, and wherein at least one crest of the thread is convexly curved.

2. The orthopedic screw of claim 1, wherein an angle greater than or equal to approximately 90 degrees is formed between each leading flank of the thread and an adjacent root of the thread.

3. The orthopedic screw of claim 1, wherein at least one leading flank of the thread is concave.

4. The orthopedic screw of claim 1, wherein an angle greater than or equal to approximately 90 degrees is formed between each trailing flank of the thread and an adjacent root of the thread.

5. The orthopedic screw of claim 1, wherein each of the plurality of teeth comprises a chamfered edge between at least one of the leading flank and the root, the trailing flank and the root, the crest and the leading flank, and the crest and the trailing flank.

6. The orthopedic screw of claim 1, further comprising at least one cutting flute in the thread, wherein the at least one cutting flute interrupts fewer than all of the plurality of teeth of the thread.

7. The orthopedic screw of claim 1, further comprising at least one cutting flute in the thread, wherein a depth of the at least one cutting flute decreases toward the proximal end of the orthopedic screw.

8. The orthopedic screw of claim 1, wherein the shaft comprises a tapered portion near the distal end of the orthopedic screw and a non-tapered portion near the proximal end of the orthopedic screw, the tapered portion of the shaft gradually widening until reaching the non-tapered portion, the tapered portion comprising at least a portion of the root of the orthopedic screw, wherein the thread extends entirely across the tapered portion of the shaft.

9. The orthopedic screw of claim 8, wherein a height of the thread gradually decreases as the tapered portion of the shaft gradually widens.

10. The orthopedic screw of claim 8, wherein the non-tapered portion of the shaft has a first outer diameter and the thread extending from the tapered portion of the shaft has a second outer diameter, the first outer diameter and the second outer diameter being equal.

11. The orthopedic screw of claim 1, wherein the crest intersects the leading flank at a first location and the trailing flank at a second location, a line between the first and second locations extending transversely to the longitudinal axis of the shaft.

12. The orthopedic screw of claim 1, wherein an angle of 10 degrees, 20 degrees, 30 degrees, 40 degrees, 50 degrees, 60 degrees, 70 degrees, 80 degrees, or more is formed between each crest and the longitudinal axis, the angle being measured proximally of each crest toward the proximal end of the orthopedic screw.

13. In combination:
the orthopedic screw of claim 1, wherein a first angle is defined between the crest and the longitudinal axis; and
a second orthopedic screw comprising a second shaft having a second longitudinal axis and a thread that extends helically from the second shaft to define a plurality of teeth, each of the plurality of teeth comprising:
a leading flank;
a trailing flank; and
a crest extending between the leading flank and the trailing flank, a second angle being defined between the crest and the second longitudinal axis of the second orthopedic screw, wherein the second angle differs from the first angle.

14. An orthopedic assembly configured to repair a bone fracture comprising:
an alignment device having a bore; and
an orthopedic screw sized to be received within the bore of the alignment device and configured to be driven into a bone, the orthopedic screw comprising:
a distal end;
a proximal end;
a shaft extending between the distal end and the proximal end of the orthopedic screw, the shaft comprising a longitudinal axis; and
a thread extending helically from the shaft to define a plurality of teeth, each of the plurality of teeth being separated by a root, and each of the plurality of teeth comprising:
a leading flank facing the distal end of the orthopedic screw;
a trailing flank facing the proximal end of the orthopedic screw; and
a crest extending between the leading flank and the trailing flank, the crest extending transversely to the longitudinal axis of the shaft, wherein each crest faces the distal end of the orthopedic screw, wherein the trailing flank extends further from the root than the leading flank, and wherein at least one crest of the thread is convexly curved.

15. The orthopedic assembly of claim 14, wherein the alignment device comprises an intramedullary nail.

16. The orthopedic assembly of claim 14, wherein an angle greater than or equal to approximately 90 degrees is formed between each leading flank of the thread and an adjacent root of the thread.

17. The orthopedic assembly of claim 14, wherein at least one leading flank of the thread is concave.

18. The orthopedic assembly of claim 14, wherein an angle greater than or equal to approximately 90 degrees is formed between each trailing flank of the thread and an adjacent root of the thread.

19. An orthopedic screw comprising:
a distal end;
a proximal end;
a shaft extending between the distal end and the proximal end of the orthopedic screw, the shaft comprising a longitudinal axis; and
a thread extending helically from the shaft to define a plurality of teeth, each of the plurality of teeth being separated by a root, and each of the plurality of teeth comprising:
a leading flank facing the distal end of the orthopedic screw;
a trailing flank facing the proximal end of the orthopedic screw; and
a crest extending between the leading flank and the trailing flank in a direction transverse to the longitudinal axis of the shaft, the crest being convexly curved from the leading flank to the trailing flank, the trailing flank extending further from the root than the leading flank such that the crest faces the distal end of the orthopedic screw.

* * * * *